United States Patent
Di Modugno et al.

(10) Patent No.: US 9,420,781 B1
(45) Date of Patent: *Aug. 23, 2016

(54) AGROCHEMICAL ADJUVANT CONCENTRATE FOR HERBICIDES

(71) Applicant: LAMBERTI SpA, Ambizzate (Varese) (IT)

(72) Inventors: Rocco Di Modugno, Spring, TX (US); James Dean Reiss, West Dundee, IL (US); Bradley Eidem, Spring, TX (US); Giovanni Floridi, Novara (IT); Giuseppe Li Bassi, Gavirate (IT)

(73) Assignee: LAMBERTI SPA, Albizzate (VA) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,385

(22) Filed: Feb. 6, 2015

(51) Int. Cl.
*A01N 25/02* (2006.01)
*A01N 25/30* (2006.01)
*A01N 57/20* (2006.01)
*A01N 37/10* (2006.01)

(52) U.S. Cl.
CPC ............... *A01N 25/02* (2013.01); *A01N 25/30* (2013.01); *A01N 37/10* (2013.01); *A01N 57/20* (2013.01)

(58) Field of Classification Search
CPC ....... A01N 25/02; A01N 25/30; A01N 57/20; A01N 37/10
USPC .................................... 504/127, 362
See application file for complete search history.

(56) References Cited

FOREIGN PATENT DOCUMENTS

WO 2010100039 A2 9/2010

OTHER PUBLICATIONS

Behrens, R. et al., "Dicamba Volatility," Weed Science, vol. 27, No. 5 (Sep. 1979), pp. 486-493.

*Primary Examiner* — Johann R Richter
*Assistant Examiner* — Courtney Brown
(74) *Attorney, Agent, or Firm* — Mossman, Kumar & Tyler, PC

(57) ABSTRACT

The present invention relates to stable aqueous adjuvant concentrate comprising a mixture of potassium salts and at least one surfactant. The invention additionally relates to sprayable diluted herbicidal formulations (tank mixes) containing the above aqueous adjuvant concentrate and at least a herbicide.

8 Claims, No Drawings

AGROCHEMICAL ADJUVANT
CONCENTRATE FOR HERBICIDES

TECHNICAL FIELD

The present invention relates to a stable aqueous agrochemical adjuvant concentrate comprising a mixture of potassium salts and at least one surfactant.

The invention additionally relates to diluted sprayable herbicidal formulations (tank mixes) containing the above aqueous adjuvant concentrate and at least a herbicide.

BACKGROUND OF THE INVENTION

Many known agrochemicals have shown to be more effective in combination than when applied individually.

Herbicides, and in particular glyphosate, are usually sprayed in combination with adjuvants which aid or modify the action of the agrochemical and/or the physical characteristics of the composition applied on the fields.

Adjuvants can be divided in different classes: activator adjuvants, such as surfactants and crop oils; utility adjuvants, such as water conditioning agents (water conditioners), antifoam agents, buffering agents and compatibility agents; and spray modifiers, such as stickers, spreader-stickers, foaming agents and drift control agents.

Among the utility adjuvants, the water conditioners help to reduce the antagonism and inactivation of some herbicides due to certain cations found in water used as the carrier. In fact hard waters contain varying levels of calcium, magnesium and iron cations, which tie up weak acid herbicides, such as 2,4-D, dicamba and glyphosate, reducing their availability.

Certain water conditioners have been shown to maintain the effectiveness of weak acid herbicides interfering with their association with the magnesium, calcium and iron ions or by binding said metal ions.

Moreover, there are some evidences that some water conditioners also contribute to more rapid uptake of the herbicide into the plant and across cell membranes through ion trapping or protonation of the herbicide molecule Several water conditioners are known in the art, perhaps the best examples being ammonium containing compounds such as ammonium sulfate (AMS), urea ammonium nitrate (UAN) and diammonium phosphate (DAP). However salts of alkali metal, such as potassiumsulfate, di-potassium phosphate, potassium nitrate, potassium citrate and the like, can be also used.

Unfortunately all water conditioners are not equal in their effectiveness, and ammonium containing compounds, and in particular AMS, remain the reference for performance.

Ammonium sulfate is effective and quite inexpensive. However, the use of ammonium sulfate sometime is problematic because the solubility of dry formulations of ammonium sulfate in water varies with variable water parameters. Water temperature, hardness and mineral content all effect the mixing of dry ammonium sulfate into the spray mixture. This unpredictable solubility is problematic for mixers and applicators of crop protection products. In fact insoluble matter can easily plug sprayer hoses, strainer, filters and nozzle tips, causing an uneven application of the spray solution. This could cause inconsistent and unacceptable control of weeds, plant disease or insects in addition to directly exposing individuals applying the spray solution to the targeted area or crop. These problems can be exacerbated when ammonium sulfate is formulated with certain types of surfactants.

Moreover the use of ammonium containing water conditioners does not appear to be ideal with all weak acid herbicides. In particular it has been found that the use of ammonium containing compounds in combination with weak acid herbicides of the auxin class, such as alts of dicamba, can produce an undesirable volatilization of the herbicide from the area of application and thus posing a risk for off-target movement and crop injury. Volatilization of auxin herbicides is known in the art, for example in Behren, R. and Lueschen, W. E., Weed Science 27, 5, 486-493 (1979); however it appears that this phenomenon is amplified when certain herbicides such as dicamba are applied in combination with ammonium containing compounds.

For these reasons, it would be advantageous to develop water conditioners, which do not contain ammonium ions and at the same time show an efficacy comparable to ammonium sulfate.

As already stated, potassium salts, such as di-potassium phosphate, potassium nitrate, potassium sulfate and tri-potassium citrate can be used as water conditioners in substitution of ammonium compounds. Unfortunately they exhibit a fairly lower efficacy than ammonium sulfate.

We have now discovered that specific mixtures of these three potassium salts show an effectiveness as water conditioner comparable ammonium sulfate and effectively protect certain pesticides from deactivation.

Aqueous concentrates of these potassium salts are stable even at low temperature and can be used in adjuvant formulations to be tank mixed with a wide range of pesticides, but in particular glyphosate and/or dicamba formulations, without showing the problems found with ammonium sulfate compositions.

DESCRIPTION OF THE INVENTION a. It is therefore an object of the present invention an aqueous adjuvant concentrate with superior water conditioning properties comprising from 15 to 45% by weight (% wt), preferably from 20 to 35% wt, of a mixture of potassium salts consisting of: from 1 to 4 parts by weight (pbw), preferably from 1.5 to 3.5 pbw, of di-potassium phosphate; from 0.5 to 1.5 pbw, preferably from 0.8 to 1.2 pbw, of potassium nitrate; and from 0.5 to 1.5 pbw, preferably from 0.8 to 1.2 pbw, of tri-potassium citrate.

b. It is another object of the present invention a diluted sprayable herbicidal formulation (tank mix) comprising from 0.01 to 20% wt, preferably from 0.01 to 5% wt of at least one herbicide and from 0.01 to 5% wt of a mixture of potassium salts consisting of: from 1 to 4 pbw, preferably from 1.5 to 3.5 pbw, of di-potassium phosphate; from 0.5 to 1.5 pbw, preferably from 0.8 to 1.2 pbw, of potassium nitrate; and from 0.5 to 1.5 pbw, preferably from 0.8 to 1.2 pbw, of tri-potassium citrate.

DETAILED DESCRIPTION OF THE INVENTION

Typically, the aqueous adjuvant concentrate of the invention comprise at least 30% by weight, preferably from 40 to 80% by weight, of water.

The aqueous adjuvant concentrate of the invention can further comprise from 0.5 to 6% wt, preferably 1 to 4% wt, of at least one surfactant, which can be chosen among anionic, cationic, non-ionic, ampholytic surfactants, and mixtures thereof.

Suitable surfactants are, for example, nonionic emulsifiers and dispersants, such as: polyalkoxylated, preferably polyethoxylated, saturated and unsaturated aliphatic alcohols, having 8 to 24 carbon atoms in the alkyl radical and having 1 to 100, preferably 4 to 40, ethylene oxide units (EO); polyalkoxylated, preferably polyethoxylated, (arylalkyl)phenols, such as, for example, tristyrylphenol having an average degree of ethoxylation of between 8 and 80, preferably between 16 and 40; polyalkoxylated, preferably polyethoxylated, alkylphenols having one or more alkyl radicals, such as, for example, nonylphenol or tri-sec-butylphenol, and a degree of ethoxylation of between 2 and 40, preferably between 4 and 20; polyalkoxylated, preferably polyethoxylated, hydroxy-fatty acids or glycerides of hydroxy-fatty acids, such as, for example, castor oil, having a degree of ethoxylation of between 10 and 80; sorbitan or sorbitol esters with fatty acids or polyalkoxylated, preferably polyethoxylated, sorbitan or sorbitol esters; polyalkoxylated, preferably polyethoxylated, amines; di- and tri-block copolymers, for example from alkylene oxides, preferably from ethylene oxide and propylene oxide, having average molar masses between 200 and 8000 g/mol, preferably between 1000 and 4000 g/mol; alkylpolyglycosides or polyalkoxylated, preferably polyethoxylated, alkylpolyglycosides.

Preferred nonionic surfactants are polyethoxylated alcohols, preferably from renewable resources, such as ethoxylated (4-8 EO) $C_{12}$-$C_{14}$ natural alcohol; polyethoxylated triglycerides of hydroxy-fatty acids and polyethylene oxide/polypropylene oxide block copolymers.

Anionic surfactants are also suitable, for example: polyalkoxylated, preferably polyethoxylated, surfactants which are ionically modified, for example by conversion of the terminal free hydroxyl function of the alkylene oxide block into a sulfate or phosphate ester; alkali metal and alkaline earth metal salts of alkylarylsulphonic acids having a straight-chain or branched alkyl chain;

alkali metal and alkaline earth metal salts of paraffin-sulfonic acids and chlorinated paraffin-sulfonic acids; polyelectrolytes, such as lignosulfonates, condensates of naphthalenesulfonate and formaldehyde, polystyrenesulfonate or sulfonated unsaturated or aromatic polymers; anionic esters of alkylpolyglycosides, such as those described in WO 2010/100039, for example alkylpolyglucoside sulfosuccinate or citrate; sulfosuccinates which are esterified once or twice with linear, or branched aliphatic, cycloaliphatic and/or aromatic alcohols, or sulfosuccinates which are esterified once or twice with (poly)alkylene oxide adducts of alcohols.

Examples of cationic and ampholytic surfactants are quaternary ammonium salts, alkyl amino acids, and betaine or imidazoline amphotensides.

Preferably the surfactant is an anionic surfactant. Preferred anionic surfactants are, in particular, salts of alkyl sulfosuccinic acids, such as sodium dioctyl sulfosuccinate, and anionic esters of alkylpolyglycosides, in particular alkylpolyglucoside citrate.

Other commonly used water conditioners can be present in the composition of the invention in an amount ranging from 0.1 to 17% wt.

Example of other water conditioners are ammonium containing compounds, such, ammonium sulfate, ammonium nitrate, ammonium hydrogen sulfate, ammonium chloride, ammonium carbonate, ammonium hydrogen carbonate, ammonium phosphate, diammonium hydrogen phosphate, ammonium dihydrogen monophosphate, ammonium sodium hydrogen phosphate, monocarbamide dihydrogensulphate and mixtures of these.

Optionally, the adjuvant concentrate also includes anti-drift agent, humectants, corrosion inhibitors, microbial inhibitors, pH adjusters, anti-foam agents or mixture thereof.

In a preferred embodiment of the present invention, the aqueous adjuvant concentrate further comprises, dissolved or dispersed, from 2 to 10% by weight, preferably 3 to 8% by weight, of an anti-drift agent.

Any anti-drift agent commonly used in the field can be used for the realization of the present invention. Preferred examples are lecithin derivatives, linear nonionic polymers with an average molecular weight of at least 20 kDa, fatty alcohol alkoxylates, water soluble polysaccharides or polysaccharide derivatives.

Suitable examples of linear nonionic polymers with an average molecular weight of at least 20 kDa are may be selected from polyacrylamide, polyacrylate, polyethylene glycol and mixture thereof.

Suitable examples of water soluble polysaccharides or polysaccharide derivatives are guar and guar derivatives, such as hydroxypropyl guar, carboxymethyl cellulose and hydroxypropyl tamarind.

Preferred anti-drift agents are hydroxypropyl guar and hydroxypropyl tamarind. Hydroxypropyl tamarind, which can be easily dissolved in these kind of concentrates, is the most preferred anti-drift agent.

In one embodiment of the invention, the pH of the adjuvant concentrate is brought to value ranging from 6.5 to 8.5, preferably from 7.0 to 8.0, by adding an appropriate amount of an acid.

Carboxylic acids, both mono- and poly-carboxylic acids, are the preferred acids that can be used to adjust the pH. Suitable examples are, without limitation, acetic acid, propanoic acid, butanoic acid, gluconic acid, lactic acid, oxalic acid, succinic acid, pyruvic acid, malic acid, malonic acid, citric acid, isocitric acid and mixtures thereof.

In a further embodiment of the invention, the aqueous adjuvant concentrate comprises a suspending agent. Any kind of suspending agent can be used for the realization of the present invention. Suitable suspending agents include, but are not limited to, hydrated fumed silica, attapulgite and bentonite clays, or their derivatives such as amine treated attapulgite clays.

Optionally, the adjuvant concentrate may also include additives commonly used in the field, such as humectants, corrosion inhibitors, microbial inhibitors, anti-foam agents, or mixture thereof.

No special or particular equipment is required for the preparation of the aqueous adjuvant concentrate of the invention. The inorganic salts and the surfactant, and optionally other additives, can be dissolved in water utilizing a common blending equipment.

The aqueous adjuvant concentrate is stable; with the term "stable" we mean that no phase separation or precipitation or gelification occur, also in difficult environmental conditions, such as high (>40° C.) or low (<10° C.) temperatures for at least one week from its preparation.

The stability of the concentrates of this invention can be further improved by mixing the dispersion under vacuum, so as to remove entrapped air.

The aqueous adjuvant concentrates of the invention have a RVT Brookfield® viscosity, at 5 rpm and 20° C., comprised between 2000 and 8000 mPa·s.

The diluted sprayable herbicide tank mixes according to the invention are obtained by adding the aqueous adjuvant concentrate to water or other suitable carrier such as, but not limited to UAN, either before or after the formulated herbicide.

Alternatively, the formulated herbicide and/or the adjuvant concentrates may be previously diluted and then mixed.

The term "diluted" is used herein with reference to herbicide active content comprised between 0.001 and 20% by weight.

Said sprayable herbicide tank mixes comprise herbicidal active compounds, such as Acetochlor, Acibenzolar, Acibenzolar-S-methyl, Acifluorfen, Acifluorfen-sodium, Aclonifen, Alachlor, Allidochlor, Alloxydinn, Alloxydinn-sodium, Ametryn, Amicarbazone, Amidochlor, Amidosulfuron, Aminocyclopyrachlor, Aminopyralid, Amitrole, Ammonium sulfamat, Ancymidol, Anilofos, Asulam, Atrazine, Azafenidin, Azimsulfuron, Aziprotryn, Beflubutamid, Benazolin, Benazolin-ethyl, Bencarbazone, Benfluralin, Benfuresate, Bensulide, Bensulfuron, Bensulfuron-methyl, Bentazone, Benzfendizone, Benzobicyclon, Benzofenap, Benzofluor, Benzoylprop, Bicyclopyrone, Bifenox, Bispyribac, Bispyribac-sodium, Bromacil, Bromobutide, Bromofenoxim, Bromoxynil, Bromuron, Buminafos, Busoxinone, Butachlor, Butafenacil, Butamifos, Butenachlor, Butralin, Butroxydim, Butylate, Cafenstrole, Carbetamide, Carfentrazone, Carfentrazone-ethyl, Chlomethoxyfen, Chloramben, Chlorazifop, Chlorazifop-butyl, Chlorbromuron, Chlorbufam, Chlorfenac, Chlorfenac-sodium, Chlorfenprop, Chlorflurenol, Chlorflurenol-methyl, Chloridazon, Chlorimuron, Chlorimuron-ethyl, Chlormequat-chloride, Chlornitrofen, Chlorophthalim, Chlorthal-dimethyl, Chlorotoluron, Chlorsulfuron, Cinidon, Cinidon-ethyl, Cinmethylin, Cinosulfuron, Clethodim (C10), Clodinafop, Clodinafop-propargyl, Clofencet, Clomazone, Clomeprop, Cloprop, Clopyralid (C1), Cloransulam, Cloransulam-methyl, Cumyluron, Cyanamide, Cyanazine, Cyclanilide, Cycloate, Cyclosulfamuron, Cycloxydim (C11), Cycluron, Cyhalofop, Cyhalofop-butyl, Cyperquat, Cyprazine, Cyprazole, 2,4-D, 2,4-DB, Dalapon, Daminozide, Dazomet, n-Decanol, Desmedipham, Desmetryn, Detosyl-Pyrazolate (DTP), Diallate, Dicamba, Dichlobenil, Dichlorprop, Dichlorprop-P, Diclofop, Diclofop-methyl, Diclofop-P-methyl, Diclosulam, Diethatyl, Diethatyl-ethyl, Difenoxuron, Difenzoquat, Diflufenican, Diflufenzopyr, Diflufenzopyr-sodium, Dimefuron, Dikegulac-sodium, Dimefuron, Dimepiperate, Dimethachlor (C2), Dimethametryn, Dimethenamid, Dimethenamid-P, Dimethipin, Dimetrasulfuron, Dinitramine, Dinoseb, Dinoterb, Diphenamid, Dipropetryn, Diquat, Diquat-dibromide, Dithiopyr, Diuron, DNOC, Eglinazine-ethyl, Endothal, EPTC, Esprocarb, Ethalfluralin, Ethametsulfuron, Ethametsulfuron-methyl, Ethephon, Ethidimuron, Ethiozin, Ethofumesate, Ethoxyfen, Ethoxyfen-ethyl, Ethoxysulfuron, Etobenzanid, F-5331, d.h. N-[2-Chloro-4-fluoro-5-[4-(3-fluoropropyl)-4, 5-dihydro-5-oxo-1H-tetrazol-1-yl]-phenyl]-ethan sulfonamide, F-7967, d.h. 3-[7-Chloro-5-fluoro-2-(trifluoromethyl)-1H-benzimidazol-4-yl]-1-methyl-6-(trifluormethyl) pyrimidin-2,4(1H,3H)-dione, Fenoprop, Fenoxaprop, Fenoxaprop-P, Fenoxaprop-ethyl, Fenoxaprop-P-ethyl (C3), Fenoxasulfone, Fentrazamide, Fenuron, Flamprop, Flamprop-M-isopropyl, Flamprop-M-methyl, Flazasulfuron, Florasulam, Fluazifop, Fluazifop-P, Fluazifop-butyl, Fluazifop-P-butyl, Fluazolate, Flucarbazone, Flucarbazone-sodium, Flucetosulfuron, Fluchloralin, Flufenacet (Thiafluamide), Flufenpyr, Flufenpyr-ethyl, Flumetralin, Flumetsulam, Flumiclorac, Flumiclorac-pentyl, Flumioxazin, Flumipropyn, Fluometuron, Fluorodifen, Fluoroglycofen, Fluoroglycofen-ethyl, Flupoxam, Flupropacil, Flupropanate, Flupyrsulfuron, Flupyrsulfuron-methyl-sodium, Flurenol, Flurenol-butyl, Fluridone, Flurochloridone, Fluroxypyr, Fluroxypyr-meptyl, Flurprimidol, Flurtamone, Fluthiacet, Fluthiacet-methyl, Fluthiamide, Fomesafen, Foramsulfuron, Forchlorfenuron, Fosamine, Furyloxyfen, Glufosinate, Glufosinate ammonium, Glyphosate, Glyphosate-diammonium, Glyphosate-isopropylammonium, Glyphosate-potassium, H-9201, d.h. O-(2,4-Dimethyl-6-nitrophenyl)-O-ethyl-isopropyl phosphoramidothioate, Halosafen, Halosulfuron, Halosulfuron-methyl, Haloxyfop, Haloxyfop-p (C4), Haloxyfop-ethoxyethyl, Haloxyfop-P-ethoxyethyl, Haloxyfop-methyl, Haloxyfop-P-methyl, Hexazinone, HW-02, d.h. 1-(Dimethoxyphosphoryl)-ethyl(2,4-dichlorophenoxy)acetate, Imazamethabenz, Imazamethabenz-methyl, Imazamox (C9), Imazamox-ammonium, Imazapic, Imazapyr, Imazapyr-isopropylammonium, Imazaquin, Imazaquin-ammonium, Imazethapyr, Imazethapyr-ammonium, Imazosulfuron, Inabenfide, Indanofan, Indaziflam, Indolacetic acid (IAA), 4-Indol-3-yl-butirric acid (IBA), Iodosulfuron, Iodosulfuron-methyl-sodium, Ioxynil, Ipfencarbazone, Isocarbamid, Isopropalin, Isoproturon, Isouron, Isoxaben, Isoxachlortole, Isoxaflutole, Isoxapyrifop, KUH-043, d.h. 3-({[5-(Difluoromethyl)-1-methyl-3-(trifluoromethyl)-1H-pyrazol-4-yl]methyl}sulfonyl)-5,5-dimethyl-4,5-dihydro-1,2-oxazole, Karbutilate, Ketospiradox, Lactofen, Lenacil, Linuron, MCPA, MCPB, MCPB-methyl, -ethyl and -sodium, Mecoprop, Mecoprop-sodium, Mecoprop-butotyl, Mecoprop-P-butotyl, Mecoprop-P-dimethylammonium, Mecoprop-P-2-ethylhexyl, Mecoprop-P-potassium, Mefenacet, Mefluidide, Mepiquat-chlorid, Mesosulfuron, Mesosulfuron-methyl, Mesosulfuron-methyl-Na, Mesotrione, Methabenzthiazuron, Metam, Metamifop, Metamitron, Metazachlor (C5), Metazasulfuron, Methazole, Methiopyrsulfuron, Methiozolin, Methoxyphenone, Methyldymron, 1-Methylcyclopropen, Methylisothiocyanat, Metobenzuron, Metobromuron, Metolachlor, S-Metolachlor, Metosulam, Metoxuron, Metribuzin, Metsulfuron, Metsulfuron-methyl, Molinate, Monalide, Monocarbamide, Monocarbamide-dihydrogensulfat, Monolinuron, Monosulfuron, Monosulfuron-ester, Monuron, MT-128, d.h. 6-Chloro-N-[(2E)-3-chloroprop-2-en-1-yl]-5-methyl-N-phenylpyridazin-3-amine, MT-5950, d.h. N-[3-Chloro-4-(1-methylethyl)-phenyl]-2-methylpentanamide, NGGC-011, Naproanilide, Napropamide (C6), Naptalam, NC-310, d.h.4-(2,4-Dichlorobenzoyl)-1-methyl-5-benzyloxypyrazole, Neburon, Nicosulfuron, Nipyraclofen, Nitralin, Nitrofen, Nitrophenolat-sodium (isomer mixture), Nitrofluorfen, Nonansäure, Norflurazon, Orbencarb, Orthosulfamuron, Oryzalin, Oxadiargyl, Oxadiazon, Oxasulfuron, Oxaziclomefone, Oxyfluorfen, Paclobutrazol, Paraquat, Paraquat-dichlorid, Pendimethalin, Pendralin, Penoxsulam, Pentanochlor, Pentoxazone, Perfluidone, Pethoxamid, Phenisopham, Phenmedipham, Phenmedipham-ethyl, Picloram, Picolinafen, Pinoxaden, Piperophos, Pirifenop, Pirifenop-butyl, Pretilachlor, Primisulfuron, Primisulfuron-methyl, Probenazole, Profluazol, Procyanine, Prodiamine, Prifluraline, Profoxydim, Prohexadione, Prohexadione-calcium, Prohydrojasmone, Prometon, Prometryn, Propachlor, Propanil, Propaquizafop, Propazine, Propham, Propisochlor, Propoxycarbazone, Propoxycarbazone-sodium, Propyrisulfuron, Propyzamide, Prosulfalin, Prosulfocarb, Prosulfuron, Prynachlor, Pyraclonil, Pyraflufen, Pyraflufen-ethyl, Pyrasulfotole, Pyrazolynate (Pyrazolate), Pyrazosulfuron, Pyrazosulfuron-ethyl, Pyrazoxyfen, Pyribambenz, Pyribambenz-isopropyl, Pyribambenz-propyl, Pyribenzoxim, Pyributicarb, Pyridafol, Pyridate (C7), Pyriftalid, Pyriminobac, Pyriminobac-methyl, Pyrimisulfan, Pyrithiobac, Pyrithiobac-sodium, Pyroxasulfone, Pyroxsulam, Quinclorac, Quinmerac, Quinoclamine, Quizalofop, Quizalofop-ethyl, Quizalofop-P, Quizalofop-P-ethyl, Quizalofop-P-tefuryl, Rimsulfuron, Saflufenacil, Secbumeton, Sethoxydim, Siduron, Simazine, Simetryn, SN-106279, d.h. Methyl-(2R)-2-({7-[2-chloro-4-(trifluoromethyl)phenoxy]-2-naphthyl}oxy) propanoate, Sulcotrione, Sulfallate (CDEC), Sulfentrazone, Sulfonneturon, Sulfonneturon-methyl, Sulfosate (Glyphosate-trimesium), Sulfosulfuron, SYN-523, SYP-249, d.h. 1-Ethoxy-3-methyl-1-oxobut-3-en-2-yl-5-[2-chloro-4-(trifluoromethyl) phenoxy]-2-nitrobenzoate, SYP-300, d.h.1-[7-Fluoro-3-oxo-4-(prop-2-in-1-yl)-3,4-dihydro-2H-1,4-benzoxazin-6-yl]-3-propyl-2-thioxoimidazolidin-4,5-dione, Tebutam, Tebuthiuron, Tecnazene, Tefuryltrione, Tembotrione, Tepraloxydim, Terbacil, Terbucarb, Terbuchlor, Terbumeton, Terbuthylazine, Terbutryn, Thenylchlor, Thiafluamide, Thiazafluron, Thiazopyr, Thidiazinnin, Thidiazuron, Thiencarbazone, Th iencarbazone-methyl, Thifensulfuron, Thifensulfuron-methyl, Thiobencarb, Tiocarbazil, Topramezone, Tralkoxydim, Triallate, Triasulfuron, Triaziflam, Triazofenamide, Tribenuron, Tribenuron-methyl, Trichloroacetic acid (TCA), Triclopyr, Tridiphane, Trietazine, Trifloxysulfuron, Trifloxysulfuron-sodium, Trifluralin (C8), Triflusulfuron, Triflusulfuron-methyl, Trimeturon, Trinexapac, Trinexapac-ethyl, Tritosulfuron, Tsitodef, Uniconazole, Uniconazole-P, Vernolate, ZJ-0862, d.h.3,4-Dichloro-N-{2-[(4,6-dimethoxypyrimidin-2-yl)oxy]benzyl}aniline, salts thereof and mixture thereof.

The adjuvant concentrates of the present invention are particularly suited for the preparation of sprayable tank mixes of N-(phosphonomethyl) glycine (Glyphosate) and its salts, Dicamba and its salts and 2-4D and its salts, and mixture thereof. Tank mixes comprising combinations of N-(phosphonomethyl) glycine and Dicamba, or salts thereof, are particularly preferred.

Other biologically active ingredients such as other pesticides, plant growth regulators, algicides, fungicides, bactericides, viricides, insecticides, acaricides, nematicides may be added as partners in the sprayable herbicidal tank mixes.

The diluted sprayable herbicidal tank mix of the invention may additionally comprise other conventional additives, including thickeners, flow enhancers, wetting agents, buffers, lubricants, fillers, drift control agents, deposition enhancers, evaporation retardants, frost protecting agents, insect attracting odor agents, UV protecting agents, fragrances, anti-foam agents and the like.

Application rates will depend upon the weeds to be controlled and the degree of control desired. In general, the formulations of this invention are most efficiently employed at a rate of 0.001 to 22.4 kilograms of the active ingredients per hectare, preferably 0.01 to 16.8 kilograms per hectare.

The diluted sprayable herbicidal tank mixes of the invention are stable and can be stored for adequate period of time prior to application without problem of crystallization and clogging of the spray nozzles.

In one embodiment, the invention is an aqueous adjuvant concentrate comprising from about 15 to about 45% by weight (% wt) of a mixture of potassium salts consisting of: a) from 1 to 4 part by weight (pbw) of di-potassium phosphate; b) from 0.5 to 1.5 pbw of potassium nitrate; c) from 0.5 to 1.5 pbw of tri-potassium citrate;

In still another embodiment, the invention is an aqueous adjuvant concentrate as described hereinabove comprising from 20 to 35% wt of said mixture of potassium salts.

In yet another embodiment the invention is an aqueous adjuvant concentrate as described hereinabove, wherein said mixture of potassium salts consists of: a. from 1.5 to 3.5 pbw of di-potassium phosphate; b. from 0.8 to 1.2 pbw of potassium nitrate; and c. from 0.8 to 1.2 pbw of tri-potassium citrate.

In another embodiment, the invention is the aqueous adjuvant concentrate as described hereinabove, further comprising from 2 to 10% by weight of an anti-drift agent.

In still another embodiment, the invention is the aqueous adjuvant concentrate as described hereinabove, wherein said anti-drift agent is hydroxypropyl tamarind.

Another embodiment of the invention is the aqueous adjuvant concentrate as described hereinabove further comprising from 0.5 to 6% wt of at least a surfactant.

In still another embodiment, the invention is the aqueous adjuvant concentrate as described hereinabove, wherein said surfactant is an anionic surfactant.

In yet another embodiment, the invention is the aqueous adjuvant concentrate as described in paragraph hereinabove wherein said anionic surfactant is chosen among alkyl sulfosuccinic acids and anionic esters of alkylpolyglycosides.

In at least one embodiment, the invention is a sprayable herbicidal formulation comprising from 0.01 to 20% wt of at least one herbicide and 0.01 to 5% wt of a mixture of potassium salts consisting of: a. from 1 to 4 part by weight (pbw) of di-potassium phosphate; b. from 0.5 to 1.5 pbw of potassium nitrate; and c. from 0.5 to 1.5 pbw of tri-potassium citrate.

In yet another embodiment, the invention is a sprayable herbicidal formulation as described hereinabove wherein the herbicide is chosen among N-(phosphonomethyl) glycine and its salts, Dicamba and its salts, and 2,4-D and its salts, and mixture thereof.

In still another embodiment, the invention is the sprayable herbicidal formulation as described hereinabove wherein the herbicide is a mixture of N-(phosphonomethyl) glycine and Dicamba, or salts thereof.

The following Examples serve to illustrate the stability of aqueous adjuvant concentrates and the effectiveness of the diluted sprayable herbicide tank mixes according to the invention.

EXAMPLES

The following raw material were used in the Examples:
Eucarol® AGE AG/EC/UP, coco polyglucoside citrate, commercialized by Lamberti S.p.A.;
HPT1, hydroxypropyl tamarind having a hydroxypropyl molar substitution (MS) of 0.58 and a RVT Brookfield® viscosity of 6,420 mPa·s (5% wt water sol., 20° C. and 20 rpm);
HPG1, hydroxypropyl guar, having a MS of 0.25 and a RVT Brookfield® viscosity of 60,600 mPa·s at 10% wt water sol., 20° C. and 20 rpm;
SAG® 1572, an antifoaming agent available from Momentive Inc.;
Citric Acid, 50% wt water solution;
Attagel® 50, attapulgite available from BASF AG;
A 10% wt stock solution was prepared by pre-dispersing 10 g of Attagel® 50 in 30 g of propylene glycol, adding 60 g of water and stirring with a mechanical blade stirrer set at about 3000 rpm. The stirring was continued until the viscosity reached a steady state indicating full activation of the attapulgite;
NIS, commercial adjuvant;
Roundup® PM, a glyphosate based herbicide available from Monsanto Company;
Clarity®, a Dicamba based herbicide available from BASF AG;
DPK 50, 50% wt water solution of di-potassium phosphate; and
AMS, ammonium sulfate powder.

Example 1-5

Different amounts of potassium salts (see Table 1) were dissolved in deionized water at room temperature under stirring.

After complete solubilization, SAGO 1572 and Emulson AGE/EC/UP were added.

The mixtures were maintained under vigorous mechanical stirring, then HPT1 or HPG1 were dissolved in the solution.

Once the natural polymers were fully hydrated, the 10% wt stock solution of Attagel 50 was added to the adjuvant concentrates of Example 1 and 2.

Tables 1 shows the amount in grams or as part by weight (pbw) of the ingredients utilized and the appearance, the cold stability (0° C. for 7 days) and the RVT Brookfield® viscosity in mPa·s, determined at 25° C. and 5 rpm, of the final solutions.

Table 1 also reports the appearance of the aqueous adjuvant concentrate after a cycle of freeze & thaw, which was conducted running 3 different cycles of freeze at 0° C. for 24 hours, followed by thaw at 54° C. for other 24 hours.

TABLE 1

| Ingredient (g) | Example 1 | Example 2 | Example 3* | Example 4* | Example 5* |
|---|---|---|---|---|---|
| Potassium salts (see below) | 25 | 25 | 26 | 20 | 20 |
| Citric acid | 5 | 5 | 11 | — | — |
| SAG 1572 | 0.05 | 0.05 | 0.05 | 0.05 | 0.05 |
| EMULSON AGE/EC/UP | 1.5 | 1.5 | 1.5 | 1.5 | 1.5 |
| ATTAGEL 50 | 0.2 | 0.3 | — | — | — |
| HPT1 | 5 | — | 7 | 6 | 5 |
| HPG1 | — | 3.5 | — | — | — |
| Deionized Water | To 100 | To 100 | To 100 | To 100 | To 100 |
| K₂HPO₄ pbw | 3 | 3 | 1 | — | — |
| KNO₃ pbw | 1 | 1 | — | 1 | — |
| Tri-Potassium Citrate pbw | 1 | 1 | — | — | 1 |
| Appearance | Stable | Stable | Stable | Stable | Stable |
| Cold Stability | Stable | Stable | Stable | Stable | Stable |
| Freeze & Thaw | Stable | Stable | Stable | Stable | Stable |
| RVT Viscosity | 2800 | 2400 | 8000 | 6800 | 5100 |

*comparative

The aqueous adjuvant concentrates are considered stable when no phase separation or precipitation or gelification occur.

Herbicidal Effectiveness Test 4 diluted sprayable herbicide tank mixes were prepared using water with an hardness of 1000 ppm, 0.25% v/v of NIS and the adjuvant concentrates of Example 1 and 3-5.

For comparative purpose, two other diluted herbicide sprayable tank mixes with two different adjuvants, AMS and DPK 50, were prepared.

The concentrations of the various adjuvants in the herbicidal formulations are reported in Tables 3 and 4.

The formulations contained, as herbicides, Roundup® PM for an application rate of 11 fl oz/a (803 ml/h) and Clarity® for an application rate of 6 fl oz/a (438 ml/h).

The formulation were applied on a multispecies system. The application parameter are reported in Table 2.

TABLE 2

| Application Method | BackPack |
|---|---|
| Application Equipment | Carnage |
| Operating Pressure, Unit | 40 psi |
| Nozzle Type | TurboTee |
| Nozzle Size | 11002 |
| Spray Volume, Unit | 8.5 gal/a |

The herbicidal performances were evaluated by awarding scores to the treated plants in comparison to untreated control plants. The evaluation scale ranges from 0% to 100% herbicidal activity. 100% activity means the complete death at least of those parts of the plant that are above ground.

The results 14 and 28 days after the treatment are reported in the following Table 3 and Table 4 respectively.

TABLE 3

| | | | W WEED | | | |
|---|---|---|---|---|---|---|
| Adjuvant | Rate | Unit | LIUSS Flax | AMASS Amaranth | HELSS Sunflower | ZEAMX Corn |
| AMS* | 8.5 | lb/100 gal | 74.3 | 75.3 | 81 | 95 |
| AMS* | 17 | lb/100 gal | 88.3 | 91 | 94.3 | 96.3 |
| EXAMPLE 1 | 1.25 | % v/v | 76.7 | 82.7 | 86 | 71.7 |
| EXAMPLE 3* | 1.25 | % v/v | 61.7 | 62.7 | 60 | 66.7 |
| EXAMPLE 4* | 1.25 | % v/v | 51.7 | 55 | 73.3 | 58.3 |
| EXAMPLE 5* | 1.25 | % v/v | 50 | 66.7 | 71.7 | 61.7 |
| DPK 50* | 2 | % v/v | 48.3 | 77 | 71.7 | 85 |

*Comparative

TABLE 3

| | | | W WEED | | | |
|---|---|---|---|---|---|---|
| Adjuvant | Rate | Unit | LIUSS Flax | AMASS Amaranth | HELSS Sunflower | ZEAMX Corn |
| AMS* | 8.5 | lb/100 gal | 76 | 79.3 | 91.7 | 95 |
| AMS* | 17 | lb/100 gal | 90 | 96 | 95 | 97 |
| EXAMPLE 1 | 1.25 | % v/v | 78.3 | 82.7 | 86 | 91.7 |
| EXAMPLE 3* | 1.25 | % v/v | 65 | 72.7 | 70 | 76.7 |
| EXAMPLE 4* | 1.25 | % v/v | 61.7 | 65 | 76.7 | 85 |
| EXAMPLE 5* | 1.25 | % v/v | 56.7 | 66.7 | 75 | 78.3 |
| DPK 50* | 2 | % v/v | 58.3 | 77 | 81.7 | 87 |

*Comparative

The diluted sprayable herbicidal formulations of the invention show an herbicidal effectiveness only slightly lower than the formulation with a comparable amount of ammonium sulfate, but clearly higher than those containing the same amount of the single potassium salts.

What is claimed is:

1. An aqueous adjuvant concentrate comprising from about 15 to about 45% by weight of a mixture of potassium salts comprising:
   a. from about 1 to about 4 parts by weight of di-potassium phosphate;
   b. from about 0.5 to about 1.5 parts by weight of potassium nitrate; and
   c. from about 0.5 to about 1.5 parts by weight of tri-potassium citrate.

2. The aqueous adjuvant concentrate of claim 1, comprising from about 20 to about 35% wt of the mixture of potassium salts.

3. The aqueous adjuvant concentrate of claim 1, wherein the mixture of potassium salts comprises:
   a. from about 1.5 to about 3.5 parts by weight of di-potassium phosphate;
   b. from about 0.8 to about 1.2 parts by weight of potassium nitrate; and
   c. from about 0.8 to about 1.2 parts by weight of tri-potassium citrate.

4. The aqueous adjuvant concentrate of claim 1, further comprising from about 2 to about 10% by weight of an anti-drift agent.

5. The aqueous adjuvant concentrate of claim 4 wherein the anti-drift agent is hydroxypropyl tamarind.

6. The aqueous adjuvant concentrate of claim 1 further comprising from about 0.5 to about 6% wt of at least one surfactant.

7. The aqueous adjuvant concentrate of claim 6 wherein the surfactant is an anionic surfactant.

8. The aqueous adjuvant concentrate of claim 7 wherein the anionic surfactant is selected from the group consisting of alkyl sulfosuccinic acids, anionic esters of alkylpolyglycosides, and combinations thereof.

* * * * *